US00PP15671P2

(12) United States Plant Patent
Westhoff

(10) Patent No.: US PP15,671 P2
(45) Date of Patent: Mar. 15, 2005

(54) ***VERBENA* PLANT NAMED 'WESVERROSE'**

(50) Latin Name: *Verbena hybrida*
Varietal Denomination: Wesverrose

(75) Inventor: Heinrich Westhoff, Südlohn (DE)

(73) Assignee: Josef + Heinrich Westhoff Gartenbau Spezialkulturen, Südlohn (DE)

( * ) Notice: Subject to any disclaimer, the term of this patent is extended or adjusted under 35 U.S.C. 154(b) by 0 days.

(21) Appl. No.: 10/859,512

(22) Filed: Jun. 1, 2004

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of *Verbena* plant named 'Wesverrose', characterized by its cascading plant habit; ovate-shaped leaves; freely flowering habit; large inflorescences; and red purple-colored flowers.

1 Drawing Sheet

Botanical classification/cultivar designation: *Verbena hybrida* cultivar Wesverrose.

BACKGROUND OF THE INVENTION

The present Invention relates to a new and distinct cultivar of *Verbena* plant, botanically known as *Verbena hybrida,* and hereinafter referred to by the name 'Wesverrose'.

The new *Verbena* is a product of a planned breeding program conducted by the Inventor in Südlohn, Germany. The objective of the program is to create new *Verbena* cultivars with cascading growth habit and attractive flower colors.

The new *Verbena* originated from a cross-pollination made by the Inventor of a proprietary selection of *Verbena hybrida* identified as code number 99FAT8, not patented, as the female, or seed, parent with a proprietary selection of *Verbena hybrida* identified as code number 99FAT03, not patented, as the male, or pollen, parent. The new *Verbena* was discovered and selected by the Inventor from within the resultant progeny from the above-mentioned cross-pollination in a controlled environment in Südlohn, Germany in 2000.

Asexual reproduction of the new cultivar by terminal cuttings in a controlled environment in Südlohn, Germany, since 2001, has shown that the unique features of this new *Verbena* are stable and reproduced true to type in successive generations of asexual reproduction.

SUMMARY OF THE INVENTION

The following traits have been repeatedly observed and are determined to be the unique characteristics of 'Wesverrose'. These characteristics in combination distinguish 'Wesverrose' as a new and distinct cultivar:

1. Cascading plant habit.
2. Ovate-shaped leaves.
3. Freely flowering habit.
4. Large inflorescences.
5. Red purple-colored flowers.

Plants of the new *Verbena* differ primarily from plants of the female parent selection in flower color as plants of the female parent selection have orange-red colored flowers. In addition, plants of the new *Verbena* have a more cascading plant habit than plants of the female parent selection.

Plants of the new *Verbena* differ primarily from plants of the male parent selection in flower size as plants of the male parent selection have smaller flowers. In addition, plants of the new *Verbena* have longer lateral branches and leaves that are more ovate in shape than plants of the male parent selection.

Plants of the new *Verbena* can be compared to plants of the cultivar Wesverdark, disclosed in U.S. Plant Pat. No. 13,847. However, in side-by-side comparisons conducted in Südlohn, Germany, plants of the new *Verbena* and the cultivar Wesverdark differed in the following characteristics:

1. Plants of the new *Verbena* had a more cascading plant habit than plants of the cultivar Wesverdark.
2. Plants of the new *Verbena* were more vigorous than plants of the cultivar Wesverdark.
3. Leaves of plants of the new *Verbena* were more broadly ovate and had shorter petioles than leaves of plants of the cultivar Wesverdark.
4. Inflorescences of plants of the new *Verbena* were more open than inflorescences of plants of the cultivar Wesverdark.
5. Plants of the new *Verbena* and the cultivar Wesverdark differed in flower coloration.

Plants of the new *Verbena* can also be compared to plants of the cultivar Scarlena, disclosed in U.S. Plant Pat. No. 12,578. However, in side-by-side comparisons conducted in Südlohn, Germany, plants of the new *Verbena* and the cultivar Scarlena differed in the following characteristics:

1. Leaves of plants of the new *Verbena* were broader than leaves of plants of the cultivar Scarlena.
2. Inflorescences of plants of the new *Verbena* were more open than inflorescences of plants of the cultivar Scarlena.
3. Plants of the new *Verbena* had larger flowers than plants of the cultivar Scarlena.
4. Plants of the new *Verbena* and the cultivar Scarlena differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph differ slightly from the color values cited in the detailed botanical description, which accurately describe the colors of the new *Verbena*.

The photograph at the left of the sheet comprises a side perspective view of a typical flowering plant of 'Wesverrose' grown in a hanging basket container.

The photograph at the right of the sheet comprises a close-up view of a typical inflorescence of 'Wesverrose'.

DETAILED BOTANICAL DESCRIPTION

The cultivar Wesverrose has not been observed under all possible environmental conditions. The phenotype may vary somewhat with variations in environment such as temperature and light intensity without, however, any variance in genotype. The aforementioned photographs and following observations and measurements describe plants grown in S ̈udlohn, Germany, under commercial practice during the spring and summer in a glass-covered greenhouse with day temperatures ranging from 20 to 25° C. and night temperatures ranging from 16 to 18° C. Cuttings were planted in 12-cm containers, pinched one time about two weeks after planting, and had been growing for about 20 weeks when the photographs and description were taken. In the following description, color references are made to The Royal Horticultural Society Colour Chart, 2001 Edition, except where general terms of ordinary dictionary significance are used.

Botanical classification: *Verbena hybrida* cultivar Wesverrose.

Parentage:

*Female, or seed, parent.*—Proprietary selection of *Verbena hybrida* identified as code number 99FAT8, not patented.

*Male, or pollen, parent.*—Proprietary selection of *Verbena hybrida* identified as code number 99FAT03, not patented.

Propagation:

*Type cutting.*—Terminal cuttings.

*Time to initiate roots.*—About 10 to 14 days at 18° C.

*Time to develop roots.*—About 21 to 23 days at 18° C.

*Root description.*—Fine.

*Rooting habit.*—Vigorous, freely branching.

Plant description:

*Form.*—Compact, outwardly spreading and trailing plant habit.

*Growth and branching habit.*—Vigorous and freely-branching with the potential for two lateral branches to develop at every node after pinching.

*Plant height.*—About 12.3 cm.

*Plant diameter or spread.*—About 50 to 60 cm.

*Lateral branches.*—Length: About 49.3 cm. Diameter: About 1.9 mm. Internode length: About 7 cm. Strength: Strong. Texture: Densely pubescent. Color: 146A.

*Foliage description.*—Arrangement: Opposite, simple. Length: About 5.1 cm. Width: About 3.1 cm. Shape: Ovate. Apex: Acute. Base: Attenuate. Margin: Crenate to dentate. Texture, upper and lower surfaces: Leathery, dull; pubescent. Venation pattern: Pinnate. Color: Developing and fully expanded foliage, upper surface: 147A. Developing and fully expanded foliage, lower surface: 147B. Venation, upper surface: 147A to 147C. Venation, lower surface: 147C. Petiole: Length: About 4.7 mm. Diameter: About 2.3 mm. Color: 147C.

Flower description:

*Flower type and habit.*—Single upright salverform flowers arranged on terminal racemes. Freely flowering with about 19 flowers and flower buds per raceme; about two racemes per lateral branch. Inflorescence is positioned above and beyond the foliage. Individual flowers last about two to four days under greenhouse conditions. Petals self cleaning; calyx and flower stalks persistent. Flowers sessile.

*Fragrance.*—None detected.

*Flowering season.*—In the garden, flowering is continuous from spring until fall.

*Inflorescence size.*—Diameter: About 7 cm. Height: About 2.9 cm.

*Flower size.*—Diameter: About 2.3 cm. Height: About 2.7 cm. Tube length: About 2.4 cm. Throat diameter: About 2.5 mm. Tube diameter, at base: About 1.7 mm.

*Flower buds.*—Length: About 1.3 to 1.5 cm. Diameter: About 3 mm. Shape: Tubular. Color: 146B; towards the apex, 54C.

*Petals.*—Quantity/arrangement: Five per flower fused at base. Petal length from throat: About 1 cm. Petal width: About 8.7 mm. Shape: Roughly cordate. Apex: Emarginate. Margin: Entire. Texture, upper and lower surfaces: Velvety, smooth. Color: When opening, upper surface: 66A. When opening, lower surface: 66D. Fully opened, upper surface: 66B; towards the base, 73D. Fully opened, lower surface: 69C and 69D. Throat: 145D. Tube: 145D.

*Sepals.*—Quantity/arrangement: Five, fused into a tube. Length: About 1.4 cm. Diameter: About 2.2 mm. Shape: Ligulate. Apex: Acute. Margin: Entire. Texture, upper and lower surfaces: Velvety, very viscid. Color, upper and lower surfaces: 146B.

*Peduncles.*—Length: About 1.5 to 2.4 cm. Diameter: About 1.6 mm. Strength: Wiry. Color: 146B.

*Reproductive organs.*—Stamens: Quantity per flower: Four. Anther shape: Two-parted, ovate. Anther length: About 1.1 mm. Anther color: 144C to 145C. Pollen amount: Scarce. Pollen color: 144D. Pistils: Quantity per flower: One. Pistil length: About 1.5 cm. Stigma shape: Ovate. Stigma color: 146A to 146B. Style length: About 1.3 cm. Style color: 145C to 145D. Ovary color: 144A to 144B.

*Fruit/seed.*—Fruit and seed production has not been observed.

Disease/pest resistance: Plants of the new *Verbena* have not been observed to be resistant to pathogens and pests common to *Verbena*.

Temperature tolerance: Plants of the new *Verbena* have been observed to be tolerant to temperatures ranging from 2 to 30° C.

It is claimed:

1. A new and distinct cultivar of *Verbena* plant named 'Wesverrose', as illustrated and described.

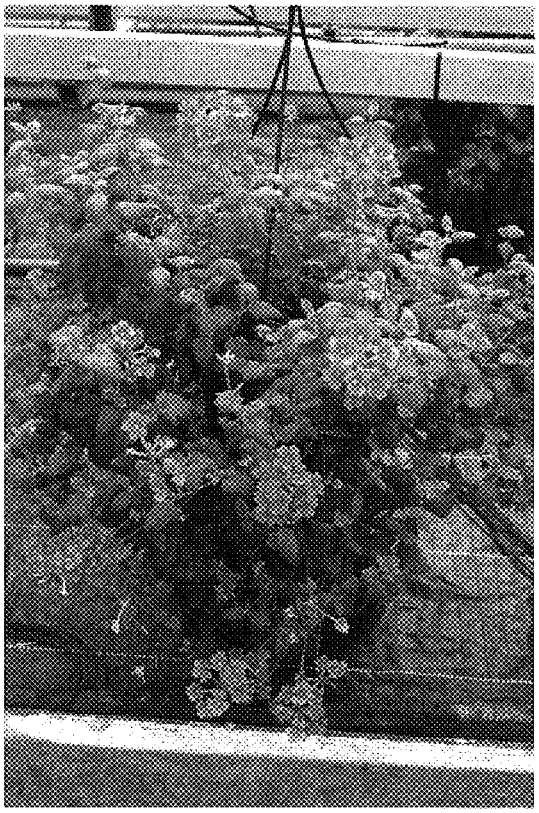
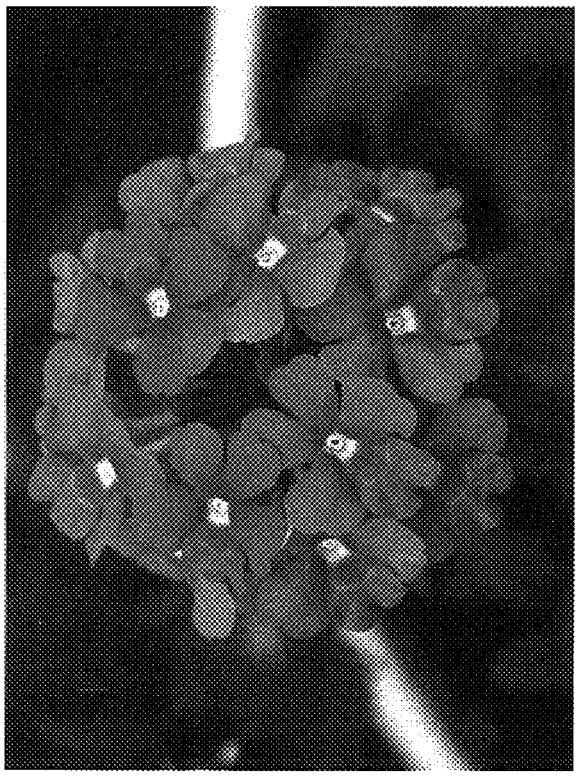

* * * * *